(12) United States Patent
Watson et al.

(10) Patent No.: US 10,314,531 B2
(45) Date of Patent: Jun. 11, 2019

(54) MONITORING COMPLIANCE USING VENOUS REFILL DETECTION

(71) Applicant: KPR U.S., LLC, Mansfield, MA (US)

(72) Inventors: Kristin L. Watson, Lithia, FL (US); Mark A. Vess, Hanson, MA (US)

(73) Assignee: KPR U.S., LLC, Mansfield, MA (US)

( * ) Notice: Subject to any disclaimer, the term of this patent is extended or adjusted under 35 U.S.C. 154(b) by 0 days.

(21) Appl. No.: 15/452,971

(22) Filed: Mar. 8, 2017

(65) Prior Publication Data
US 2017/0196502 A1    Jul. 13, 2017

Related U.S. Application Data

(63) Continuation of application No. 12/894,826, filed on Sep. 30, 2010.

(51) Int. Cl.
| | |
|---|---|
| *A61B 5/103* | (2006.01) |
| *A61B 5/00* | (2006.01) |
| *A61B 5/026* | (2006.01) |
| *A61H 9/00* | (2006.01) |

(Continued)

(52) U.S. Cl.
CPC ............ *A61B 5/4833* (2013.01); *A61B 5/026* (2013.01); *A61B 5/6802* (2013.01); *A61B 5/6828* (2013.01); *A61B 5/7275* (2013.01); *A61H 9/0078* (2013.01); *G06F 19/00* (2013.01); *A61B 5/022* (2013.01); *A61H 2201/0184* (2013.01); *A61H 2201/164* (2013.01); *A61H 2201/5007* (2013.01); *A61H 2201/5069* (2013.01); *A61H 2201/5071* (2013.01); *A61H 2205/10* (2013.01); *A61H 2209/00* (2013.01)

(58) Field of Classification Search
CPC ... A61B 5/4833; A61B 5/7275; A61B 5/6802; A61B 5/6828; A61B 5/026; A61B 5/022; A61H 9/0078; A61H 2201/5069; A61H 2201/0184; A61H 2205/10; A61H 2201/164; A61H 2201/5007; A61H 2201/5071
See application file for complete search history.

(56) References Cited

U.S. PATENT DOCUMENTS

| | | |
|---|---|---|
| 3,866,604 A | 2/1975 | Curless et al. |
| 4,016,868 A | 4/1977 | Allison |
| 4,353,359 A | 10/1982 | Milbauer |

(Continued)

FOREIGN PATENT DOCUMENTS

| | | |
|---|---|---|
| CN | 201516113 U | 6/2010 |
| EP | 0898475 B1 | 8/2002 |

(Continued)

OTHER PUBLICATIONS

Bogatin, "PCB Directions," Printed Circuit Design & Manufacture, Oct. 2003, vol. 20, Issue 10, Atlanta, GA, 1 page.

(Continued)

*Primary Examiner* — Rene T Towa
(74) *Attorney, Agent, or Firm* — Jacob R. Lenzke

(57) ABSTRACT

Monitoring patient compliance with a compression therapy regimen. Venous Refill Time (VRT) is monitored via a pressure sensor in a bladder of a compression system. A controller of the compression system correlates the monitored VRT to a predetermined threshold to determine whether the patient is using the compression system.

13 Claims, 14 Drawing Sheets

(51) Int. Cl.
*G06F 19/00* (2018.01)
*A61B 5/022* (2006.01)

(56) References Cited

U.S. PATENT DOCUMENTS

| | | |
|---|---|---|
| 4,396,010 A | 8/1983 | Arkans |
| 4,469,099 A | 9/1984 | McEwen |
| 4,492,234 A | 1/1985 | Arkans |
| 4,605,010 A | 8/1986 | McEwen |
| 4,671,290 A | 6/1987 | Miller et al. |
| 4,679,144 A | 7/1987 | Cox et al. |
| 4,686,998 A | 8/1987 | Robbins |
| 5,010,893 A | 4/1991 | Sholder |
| 5,020,527 A | 6/1991 | Dessertine |
| 5,050,613 A | 9/1991 | Newman et al. |
| 5,052,375 A | 10/1991 | Stark et al. |
| 5,103,833 A | 4/1992 | Apple |
| 5,167,237 A | 12/1992 | Rabin et al. |
| 5,233,987 A | 8/1993 | Fabian et al. |
| 5,284,133 A | 2/1994 | Burns et al. |
| 5,307,791 A | 5/1994 | Senoue et al. |
| 5,331,548 A | 7/1994 | Rollema et al. |
| 5,337,750 A | 8/1994 | Walloch |
| 5,339,825 A | 8/1994 | McNaughton et al. |
| 5,443,440 A | 8/1995 | Tumey et al. |
| 5,459,700 A | 10/1995 | Jacobs |
| 5,474,083 A | 12/1995 | Church et al. |
| 5,514,079 A | 5/1996 | Dillon |
| 5,575,762 A | 11/1996 | Peeler et al. |
| 5,591,200 A | 1/1997 | Cone et al. |
| 5,622,180 A | 4/1997 | Tammi et al. |
| 5,718,232 A | 2/1998 | Raines et al. |
| 5,769,801 A | 6/1998 | Tumey et al. |
| 5,800,458 A * | 9/1998 | Wingrove ............... A61N 1/08 607/2 |
| 5,806,512 A | 9/1998 | Abramov et al. |
| 5,810,735 A | 9/1998 | Halperin et al. |
| 5,840,049 A | 11/1998 | Tumey et al. |
| 5,843,007 A | 12/1998 | McEwen et al. |
| 5,929,782 A | 7/1999 | Stark et al. |
| 5,968,073 A | 10/1999 | Jacobs |
| 5,982,285 A | 11/1999 | Bueche et al. |
| 6,047,203 A | 4/2000 | Sackner et al. |
| 6,051,016 A | 4/2000 | Mesaros et al. |
| 6,102,874 A | 8/2000 | Stone et al. |
| 6,135,106 A | 10/2000 | Dirks et al. |
| 6,171,270 B1 | 1/2001 | Gau |
| 6,188,407 B1 | 2/2001 | Smith et al. |
| 6,200,265 B1 | 3/2001 | Walsh et al. |
| 6,231,532 B1 * | 5/2001 | Watson ............... A61H 9/0078 601/148 |
| 6,338,719 B1 | 1/2002 | Drzewiecki et al. |
| 6,381,482 B1 | 4/2002 | Jayaraman et al. |
| 6,387,065 B1 | 5/2002 | Tumey |
| 6,416,471 B1 | 7/2002 | Kumar et al. |
| 6,436,058 B1 | 8/2002 | Krahner et al. |
| 6,440,093 B1 | 8/2002 | McEwen et al. |
| 6,450,981 B1 | 9/2002 | Shabty et al. |
| 6,468,237 B1 | 10/2002 | Lina |
| 6,514,200 B1 | 2/2003 | Khouri |
| 6,527,711 B1 | 3/2003 | Stivoric et al. |
| 6,544,202 B2 | 4/2003 | McEwen et al. |
| 6,551,252 B2 | 4/2003 | Sackner et al. |
| 6,616,579 B1 | 9/2003 | Reinbold et al. |
| 6,736,787 B1 | 5/2004 | McEwen et al. |
| 6,775,577 B2 | 8/2004 | Crnkovich et al. |
| 6,926,667 B2 | 8/2005 | Khouri |
| 6,953,440 B2 | 10/2005 | Porrata et al. |
| 7,115,104 B2 | 10/2006 | Van Brunt et al. |
| 7,118,534 B2 | 10/2006 | Ward et al. |
| 7,125,383 B2 | 10/2006 | Hoctor et al. |
| 7,207,959 B1 | 4/2007 | Chandran |
| 7,214,192 B2 | 5/2007 | Poliac et al. |
| 7,244,225 B2 | 7/2007 | Loeb et al. |
| 7,354,411 B2 | 4/2008 | Perry et al. |
| 7,395,109 B2 | 7/2008 | Drakulic |
| 7,398,803 B2 | 7/2008 | Newton |
| 7,410,475 B2 | 8/2008 | Krensky et al. |
| 7,425,203 B2 | 9/2008 | Van Brunt et al. |
| 7,426,157 B2 | 9/2008 | Arnold et al. |
| 7,593,765 B2 | 9/2009 | Rapoport et al. |
| 7,618,384 B2 | 11/2009 | Nardi et al. |
| 7,637,879 B2 | 12/2009 | Barak et al. |
| 7,909,786 B2 | 3/2011 | Bonnefin et al. |
| 7,947,003 B2 | 5/2011 | Bonnefin et al. |
| 8,025,632 B2 | 9/2011 | Einarsson |
| 8,128,584 B2 | 3/2012 | Brown |
| 8,257,289 B2 | 9/2012 | Vess |
| 8,578,939 B1 | 11/2013 | Kimani Mwangi et al. |
| 8,630,699 B2 | 1/2014 | Baker et al. |
| 9,044,372 B2 | 6/2015 | Wild et al. |
| 2002/0045804 A1 | 4/2002 | Christopherson et al. |
| 2002/0087054 A1 | 7/2002 | Lin et al. |
| 2003/0078528 A1 | 4/2003 | Rahman et al. |
| 2003/0125649 A1 | 7/2003 | McIntosh et al. |
| 2003/0135127 A1 | 7/2003 | Sackner et al. |
| 2003/0216651 A1 | 11/2003 | Burns et al. |
| 2004/0030270 A1 | 2/2004 | Johnson |
| 2004/0054306 A1 | 3/2004 | Roth et al. |
| 2004/0127937 A1 | 7/2004 | Newton |
| 2004/0199232 A1 | 10/2004 | Wallace et al. |
| 2005/0033351 A1 | 2/2005 | Newton |
| 2005/0107725 A1 | 5/2005 | Wild et al. |
| 2005/0159690 A1 | 7/2005 | Barak et al. |
| 2006/0058716 A1 | 3/2006 | Hui et al. |
| 2006/0122544 A1 | 6/2006 | Ciluffo |
| 2007/0010749 A1 | 1/2007 | Meng |
| 2007/0049853 A1 | 3/2007 | Adams et al. |
| 2007/0083152 A1 | 4/2007 | Williams, Jr. et al. |
| 2007/0088239 A1 | 4/2007 | Roth et al. |
| 2007/0173886 A1 | 7/2007 | Rousso et al. |
| 2007/0249977 A1 | 10/2007 | Bonnefin et al. |
| 2008/0033307 A1 | 2/2008 | Baudoin et al. |
| 2008/0177159 A1 | 7/2008 | Gavriely |
| 2008/0183095 A1 | 7/2008 | Austin et al. |
| 2008/0188781 A1 | 8/2008 | Carkner et al. |
| 2008/0281630 A1 | 11/2008 | Sekura |
| 2008/0312522 A1 | 12/2008 | Rowlandson et al. |
| 2009/0005703 A1 | 1/2009 | Fasciano |
| 2009/0024062 A1 | 1/2009 | Einarsson |
| 2009/0036786 A1 | 2/2009 | Gough et al. |
| 2009/0048525 A1 | 2/2009 | Rogers et al. |
| 2009/0063194 A1 | 3/2009 | Rosneck et al. |
| 2009/0234265 A1 | 9/2009 | Reid, Jr. et al. |
| 2009/0259169 A1 | 10/2009 | Loori et al. |
| 2011/0190675 A1 * | 8/2011 | Vess ............... A61H 9/0092 601/152 |
| 2012/0083712 A1 | 4/2012 | Watson et al. |
| 2013/0231596 A1 | 9/2013 | Hornbach et al. |

FOREIGN PATENT DOCUMENTS

| | | | |
|---|---|---|---|
| EP | 1645254 A1 | 4/2006 | |
| EP | 2359785 A1 | 8/2011 | |
| JP | 08280635 A | 10/1996 | |
| JP | 2008114048 A | 5/2008 | |
| WO | 00/00155 A1 | 1/2000 | |
| WO | 03/007855 A1 | 1/2003 | |
| WO | 2004062724 A1 | 7/2004 | |
| WO | 2006043080 A1 | 4/2006 | |
| WO | 2007041806 A1 | 4/2007 | |
| WO | 2011112442 A1 | 9/2011 | |
| WO | 2016/055992 A1 | 4/2016 | |

OTHER PUBLICATIONS

Gungor et al., "A New Micro-Controller based Wear-Time Monitor for Use with Removable Orthodontic Appliances", Proceedings of the 19th Annual International Conference—IEEE/EMBS, Oct. 30 thru Nov. 2, 1997. Chicago, IL, USA. 3 pages.

Kadiallah et al, "Impedance Control is Tuned to Multiple Directions of Movement," Conference Proceedings: Annual International Con-

(56) References Cited

OTHER PUBLICATIONS ference of the IEEE Engineering in Medicine & Biology Society, 2008:5358-61, Aug. 2008, 4 pages.
Prance, "Novel Sensor Enables Remote Biometric-Data Acquisition," Department of Engineering and Design—University of Sussex, 2008 SPIE, 2 pages.
SCD Response Compression System Controller. http://www.kendallvasculartherapy.com/VascularTherapy/ . . . Feb. 9, 2009, 1 page.
"Doctor Life Health Care". www.dsmaref.com as known as 2010, 41 pgs.
Aircast Inc., VenaFlow Operator's Manual, Apr. 4, 2001. 26 pgs.
"Compression Devices" www.mweb.com. vol. 67, No. 2, Feb. 2004. 2 pgs.
Orthofix Vascular Novamedix, "Take a step into the world of foot impulse technology" www.orthofix.com/avimpulse. as known as 2008, 4 pgs.
Tyco/Healthcare KENDALL, "SCD Express Compression System". as known as 2001, 24 pgs.
Patel et al., "Detecting Human Movement by Differential Air Pressure Sensing in HVAC System Ductwork: An Exploration in Infrastructure Mediated Sensing," Proceeding Pervasive '08 Proceedings of the 6th International Conference on Pervasive Computing, Sydney, Australia—May 19-22, 2008, 18 pages.
Asada, H. Harry, et al., "Mobile Monitoring with Wearable Photoplethysmographic Biosensors", IEEE Engineering in Medicine and Biology Magazine, May/Jun. 2003, 13 pages.
Breault, Martine, "A Biomechanical Investigation of Blood Flow Occlusion Achieved With the Use of Surgical Pneumatic Tourniquets", B.A.Sc., McGill University, Montreal, 1985, University of British Columbia, Oct. 1988, 252 pages.
Coppin, Rhiannon, et al., "Functional Specifications for an Infant Monitoring System", http://www.sfu.ca/~rtrost/zentech, Feb. 16, 1999, 24 pages.
Côté, MD Johanne et al., "Compliance With Peak Expiratory Flow Monitoring in Home Management of Asthma", Clinical Investigations, CHEST / 113 / 4 / Apr. 1998, 5 pages.
Fahrenberg, J. & Myrtek, M (Eds.), "Origins and Developments of Ambulatory Monitoring and Assessment", Progress in Ambulatory Assessment, Computer-assisted Psychological and Psychophysiological Methods in Monitoring and Field Studies, Forschungsgruppe Psychophysiologie, Department of Psychology, University of Freiburg, Germany Chapter 35, 2001, pp. 587-616, 30 pages.
Felton, Kevin, CO, LO, "The Use of Adherence Monitors with Orthoses", JPO 1999; vol. 11, No. 4, p. 98, 3 pages.
Finkelstein, Joseph, et al., "Home Automated Telemanagement (HAT) System to Facilitate Self-Care of Patients with Chronic Diseases", Medical Information Systems Unit, Boston University, Boston, MA, Systemics, Cybernetics and Informatics, 2003, vol. 1, No. 3, 5 pages.
Havey, Robert, BS, et al., "A Reliable and Accurate Method for Measuring Orthosis Wearing Time", SPINE vol. 27, No. 2, pp. 211-214, © 2002, Lippincott Williams & Wilkins, Inc., 4 pages.
Lou, E., et al., "The daily force pattern of spinal orthoses in subjects with adolescent idiopathic scoliosis", Prosthetics and Orthotics International, 2002, 26, 58-63, 6 pages.
Scanlon, Michael V., "Acoustic Sensor for Health Status Monitoring", Army Research Laboratory, Night Vision and Electronic Sensors Directorate, Security Team, 1998, 10221 Burbeck Rd., Ft. Belvoir, VA22060-5806, 19 pages.
Verschelden, P., et al., "Compliance with and accuracy of daily self-assessment of peak expiratory flows (PEF) in asthmatic subjects over a three month period", European Respiratory Journal, 1996, 9, pp. 880-885, 6 pages.
Office action dated Feb. 17, 2012 in related U.S. Appl. No. 12/894,826, 13 pages.
Response filed May 10, 2012 to Office Action dated Feb. 17, 2012 in related U.S. Appl. No. 12/894,826, 9 pages.
Office action dated Jul. 23, 2012 in related U.S. Appl. No. 12/894,826, 11 pages.
Response filed Sep. 24, 2012 to Office Action dated Jul. 23, 2012 in related U.S. Appl. No. 12/894,826, 5 pages.
Appeal brief dated Dec. 26, 2012 in related U.S. Appl. No. 12/894,826, 14 pages.
Examiner's answer dated Mar. 22, 2013 to Appeal brief dated Dec. 26, 2012 in related U.S. Appl. No. 12/894,826, 20 pages.
Reply brief dated May 21, 2013 to Examiner's answer dated Mar. 22, 2013 in related U.S. Appl. No. 12/894,826, 6 pages.
Decision of appeal dated Mar. 17, 2016 in related U.S. Appl. No. 12/894,826, 7 pages.
Office action dated Aug. 12, 2016 in related U.S. Appl. No. 12/894,826, 5 pages.
Response filed Nov. 10, 2016 to Office Action dated Aug. 12, 2016 in related U.S. Appl. No. 12/894,826, 9 pages.
English Translation of Notice of Reasons for Rejection dated Mar. 1, 2013 in related Japanese patent application No. 2011-215391, 6 pages.
English Translation of Office Action dated Nov. 26, 2013 in related Chinese Patent Application No. 201110303696.1, 5 pages.
Office Action dated May 6, 2014 in related Australian Patent Application No. 2013201701, 3 pages.
Office Action with English Translation of Office Action dated Aug. 3, 2016 in related Chinese Application No. 201410555763.2, 11 pages.
European Search Report for Application No. EP11182113, dated on Jan. 20, 2012, 4 pages.
European Search Report for Application No. EP13187415, dated on Jan. 14, 2014, 4 pages.
Patel, Shwetak N., et al., "Detecting Human Movement by Differential Air Pressure Sending in HVAC System Ductwork: An Exploration in Infrastructure Mediated Sensing", College of Computing, School of Interactive computing, !!. GVU Center, Georgia Institute of Technology, Springer-Verlag Berlin Heidelberg, 2008, 18 pages.

\* cited by examiner

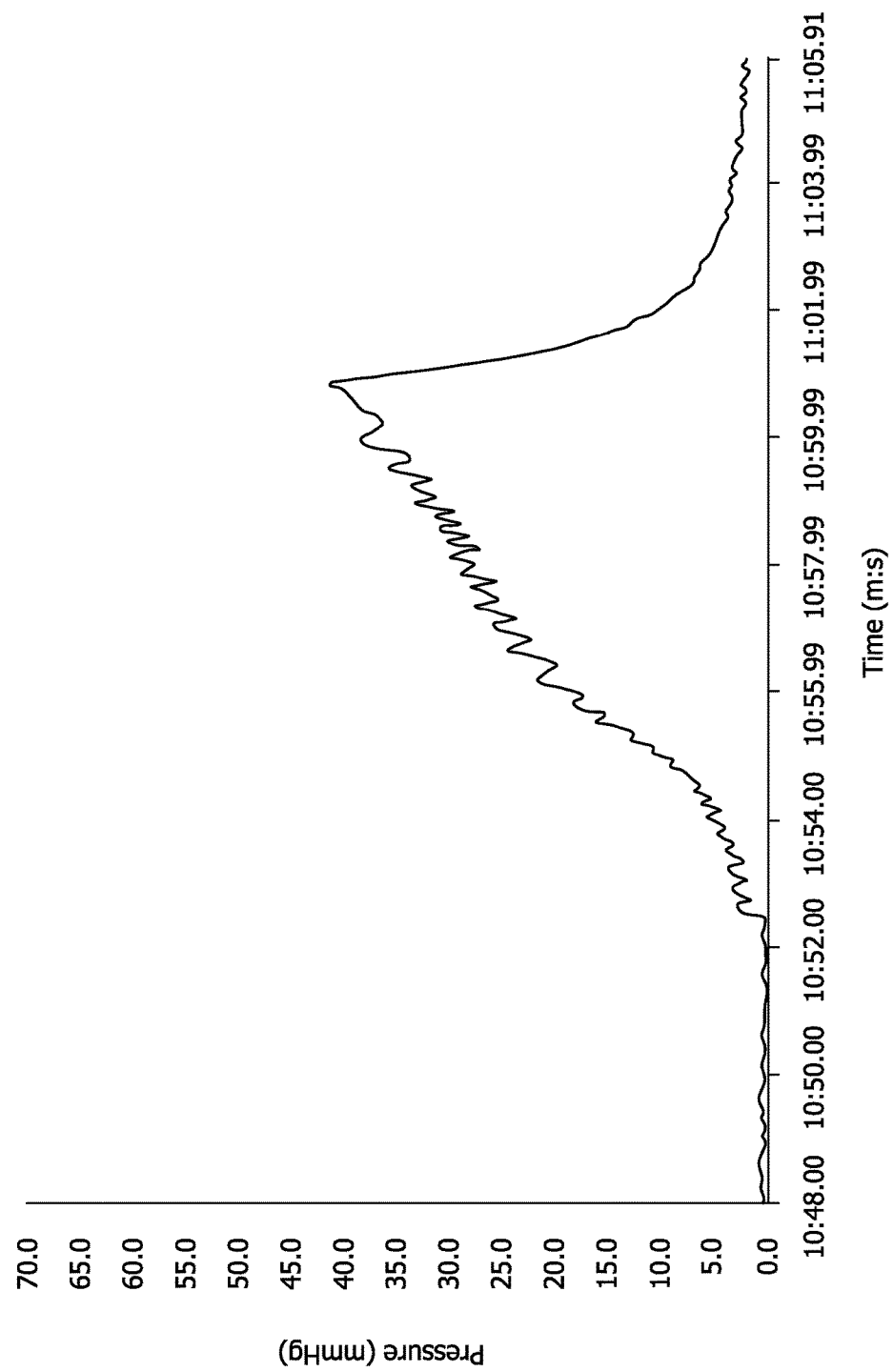

MONITORING COMPLIANCE USING VENOUS REFILL DETECTION

CROSS-REFERENCE TO RELATED APPLICATION

This application is a continuation of U.S. Ser. No. 12/894,826, filed Sep. 30, 2010, the entire contents of which is incorporated herein by reference.

BACKGROUND

Aspects of the present invention generally relate to compression garments, and particularly to monitoring use of compression garments.

A major concern for immobile patients and like persons are medical conditions that form clots in the blood, such as, deep vein thrombosis (DVT) and peripheral edema. Such patients and persons include those undergoing surgery, anesthesia, extended periods of bed rest, etc. These blood clotting conditions generally occur in the deep veins of the lower extremities and/or pelvis. These veins, such as the iliac, femoral, popliteal and tibial return, deoxygenated blood to the heart. For example, when blood circulation in these veins is retarded due to illness, injury or inactivity, there is a tendency for blood to accumulate or pool. A static pool of blood may lead to the formation of a blood clot. A major risk associated with this condition is interference with cardiovascular circulation. Most seriously, a fragment of the blood clot can break loose and migrate. A pulmonary emboli can form from the fragment potentially blocking a main pulmonary artery, which may be life threatening. The current invention can also be applied to the treatment of other conditions, such as lymphedema.

Conventional vascular compression systems include a compression sleeve or garment fluidly connected to a controller for cyclically inflating the sleeve. The sleeve wraps around a patient's limb and has one or more chambers, or bladders, inflated to provide compressive pulses to the limb, typically starting around the most distal portion of the limb (e.g., the ankle) and progressing sequentially toward the heart. The cyclical inflation of the compression garment enhances blood circulation and decreases the likelihood of DVT. Also, vascular compression systems may be applied to the treatment of other conditions, such as lymphedema.

An important monitoring parameter for compression systems is the venous refilling time (VRT) calculated by the controller, which is the normal time taken for the veins in the limb to distend with blood after compression. Current devices, such as those disclosed in U.S. Pat. No. 6,231,532, detect pressure change (e.g., via a pressure sensor) in the sleeve as a function of the change in girth of the limb to measure VRT. In turn, the controller adjusts the cycle of compressive pulses accordingly based on the calculated VRT.

Patient compliance with a prescribed compression regimen and usage of a compression system is a common problem. Unfortunately, it is nearly impossible in a health service setting for a medical professional to constantly monitor a patient during use of the system. Therefore a need exists for improved compliance monitoring.

SUMMARY

In general, aspects of the invention relate monitoring a patient's compliance with a compression therapy regimen based on a determined VRT. In one aspect, a signal is received from a pressure sensor coupled to a compression garment that is sized and shaped to be wrapped around substantially a limb of a wearer. The signal is indicative of a change of girth of the limb. A venous refill time of the limb is determined as a function of the received signal and monitored. When the monitored venous refill time exceeds a predetermined threshold, a patient compliance timer is incremented.

A system embodying aspects of the invention monitors patient compliance with a compression therapy regimen. The system includes a compression garment, a compression control unit, and a pressure sensor. The garment is sized and shaped to be wrapped around substantially a body part of a wearer and has one or more fasteners for use in securing the garment in a self-retaining wrapped configuration around the body part. And the garment comprises one or more selectively inflatable bladders for applying compression to the body part upon inflation. The compression control unit comprises a pump for pressurizing fluid and an outlet port in fluid communication with the pump. The outlet port has fluid tubing connected thereto for selectively delivering pressurized fluid to at least one of the inflatable bladders. The pressure sensor is coupled to at least one of the bladders and generates a signal indicative of a change of girth of the body part when the garment is in the wrapped configuration. The control unit also includes one or more processors receiving and responsive to the signal generated by the pressure sensor for determining a venous refill time of the body part. The processor monitors the determined venous refill time and increments a patient compliance timer in response to the monitored venous refill time exceeding a predetermined threshold.

In another aspect, a method of monitoring patient compliance with a compression therapy regimen includes receiving a signal from a pressure sensor coupled to a compression garment. The signal is indicative of a change of girth of a limb when a compression garment is wrapped substantially around the limb. The method includes determining a venous refill time of the limb as a function of the received signal and monitoring the determined venous refill time. The monitored venous refill time is compared to a predetermined range of normal venous refill times. The method also includes correlating the monitored venous refill time to determine patient compliance as a function of the comparing.

Other objects and features will be in part apparent and in part pointed out hereinafter.

BRIEF DESCRIPTION OF THE DRAWINGS

FIG. 8A is a graph illustrating an exemplary pressure cycle of an inflatable bladder when not in use;

Corresponding reference characters indicate corresponding parts throughout the drawings.

DETAILED DESCRIPTION

Figure 1:
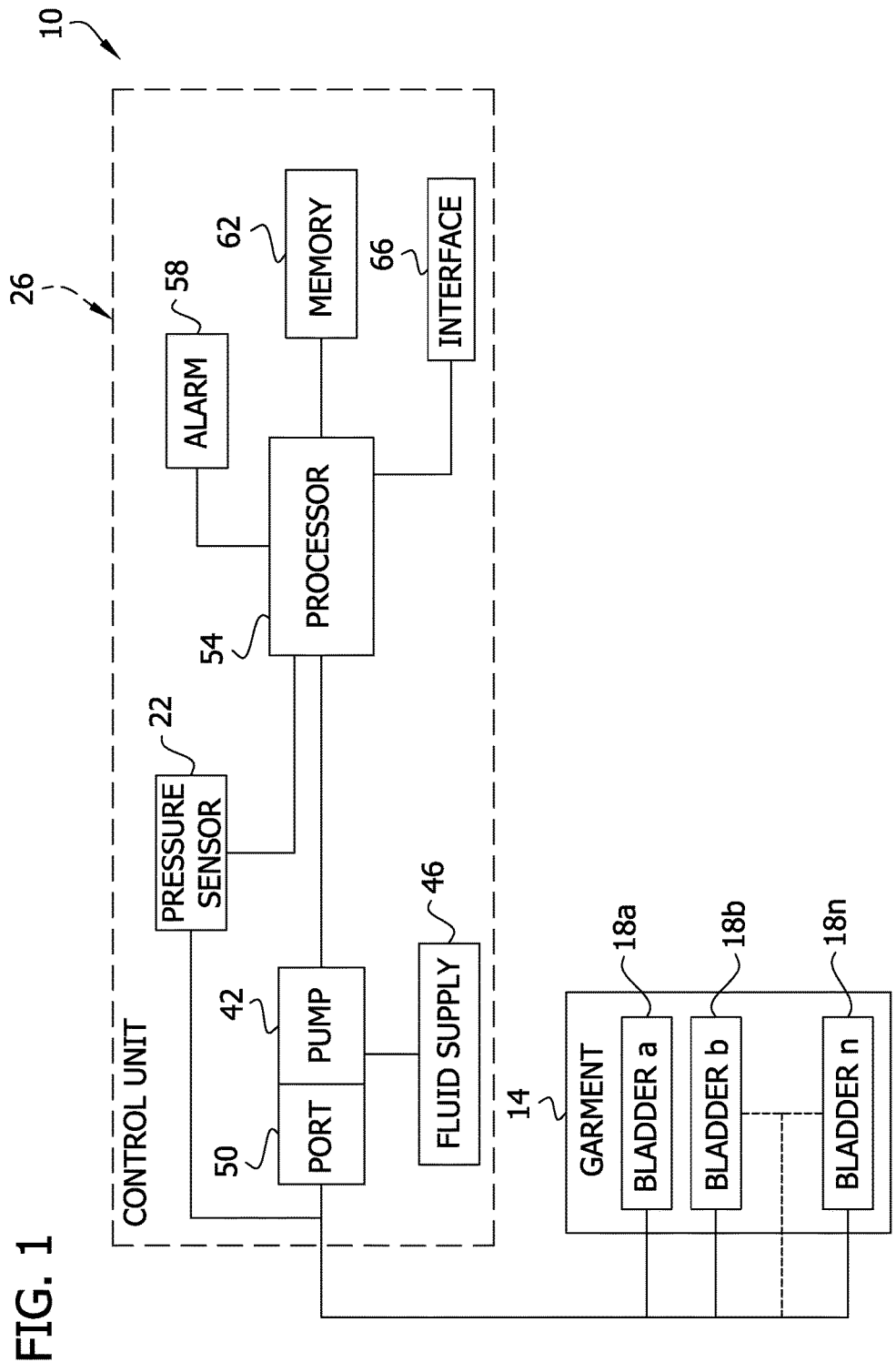
FIG. 1 is a schematic of a system for monitoring patient compliance with a compression therapy regimen.

Referring to FIG. 1, a compression therapy system for monitoring patient compliance is designated generally by the reference character 10. In an embodiment, system 10 is an intermittent pneumatic compression (IPC) device or the like. The system 10 comprises a garment 14 that can be fitted to a limb or other body part of a patient. The garment 14 has with one or more bladders 18a-n for applying compression to the limb during inflation of the bladders. The system 10 also includes a pressure sensor 22 coupled to at least one of the bladders (e.g., bladder 18b) via, for example, connection tubing, and a compression control unit 26. The control unit 26 monitors patient compliance with a prescribed compression therapy regimen. Specifically, and as will be described in detail later, control unit 26 determines, or calculates, a venous refill time (VRT) of the limb based on pressure measurements obtained from the pressure sensor 22. The control unit 26 monitors the determined VRT and increments an active therapy time or timer if the monitored VRT exceeds a predetermined threshold.

Figure 2A:
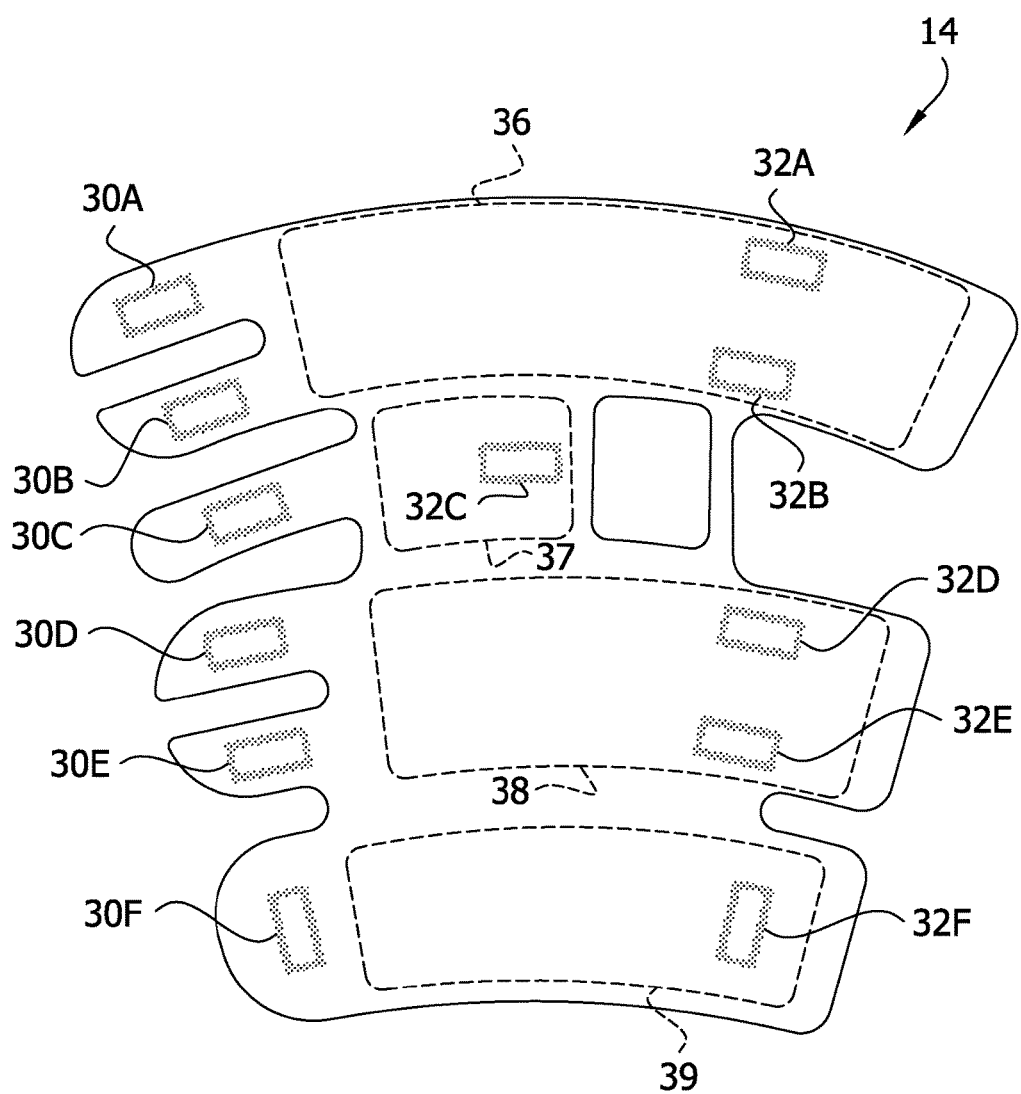
FIG. 2A is a front view of a compression garment in an unwrapped configuration.
Figure 2B:
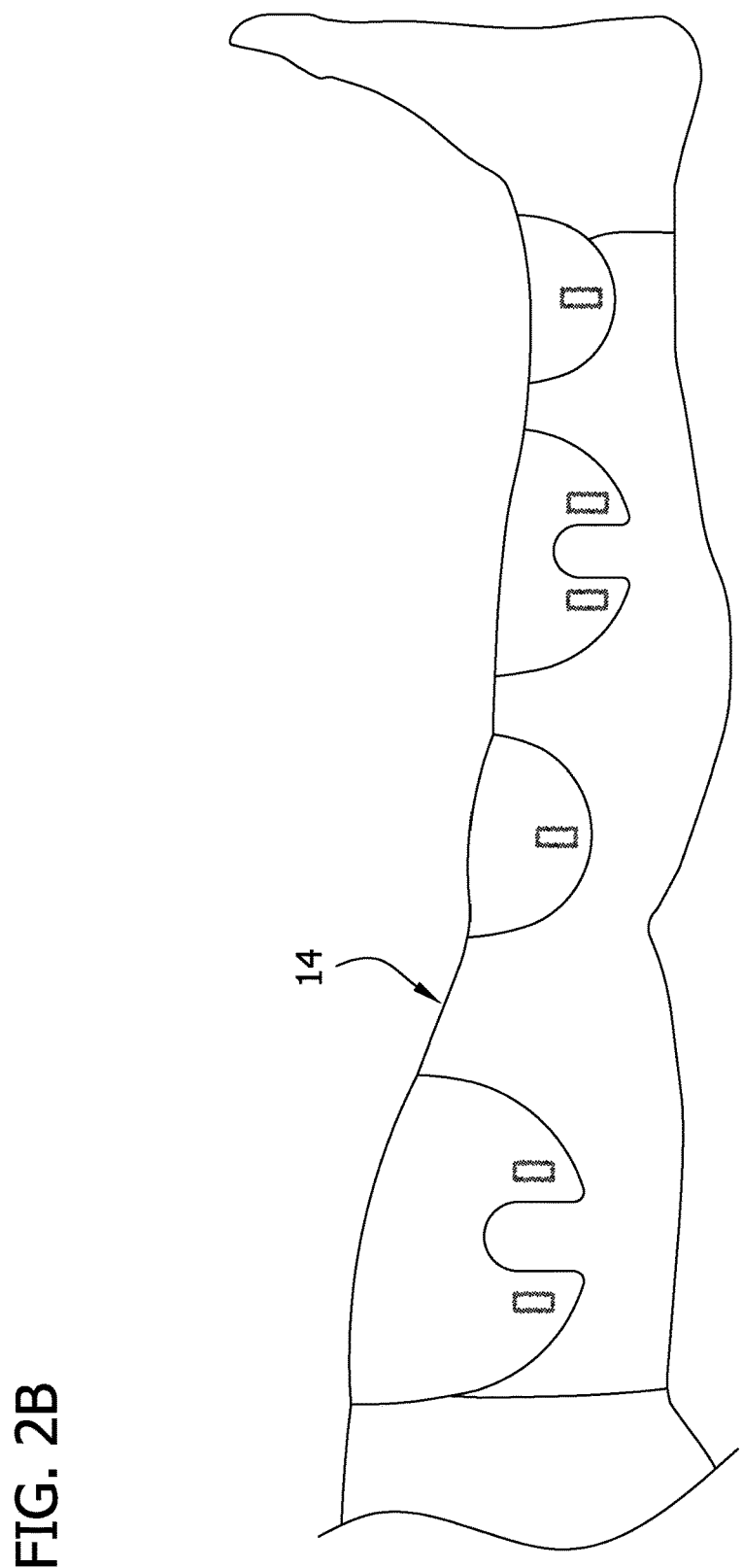
FIG. 2B illustrates the compression garment of FIG. 2A in a wrapped configuration adapted for use on a patient.
Figure 3A:
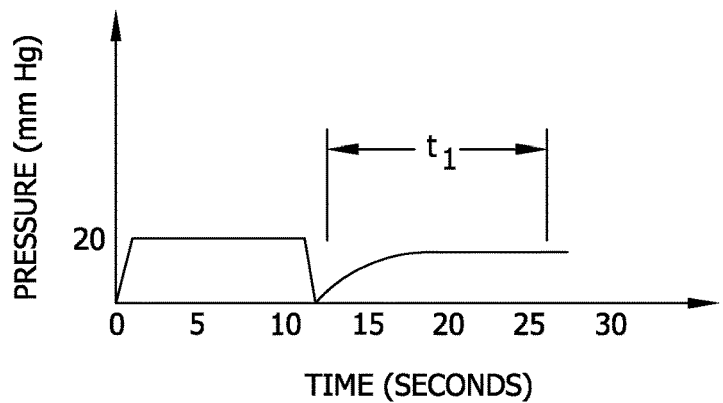
FIGS. 3A-3E are graphs illustrating exemplary pressure profiles during a procedure to determine venous refill time according to the present invention.
Figure 3B:
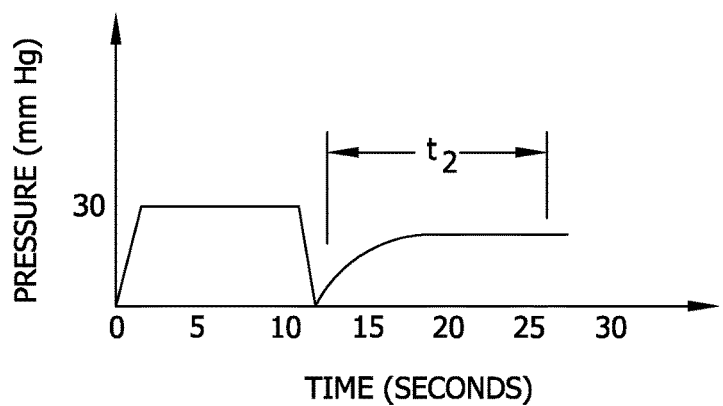
Figure 3C:
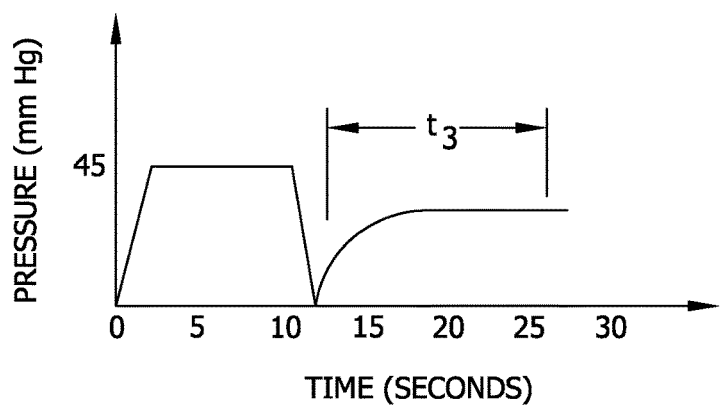
Figure 3D:
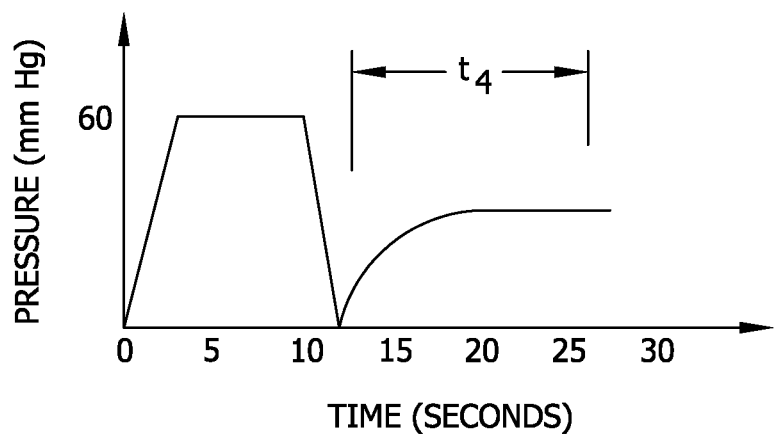
Figure 3E:
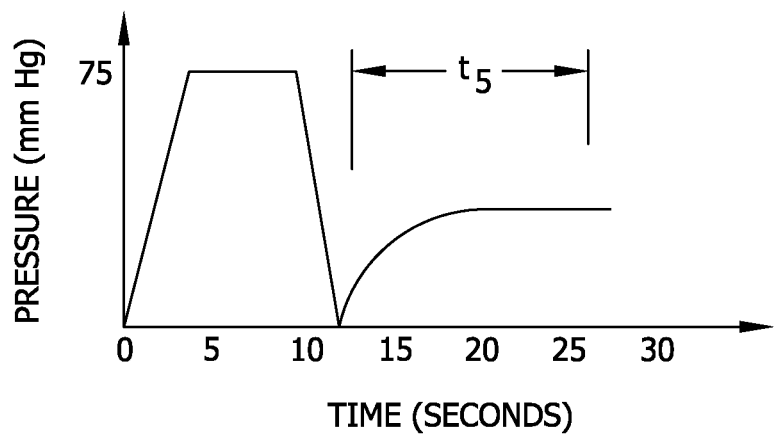

The garment 14, an exemplary embodiment of which is shown in FIGS. 2A-B without any interconnections to the rest of system 10, wraps substantially around a limb or body part of the patient. The garment 14 has one or more positioning or fitting devices, such as fasteners 30A-F, 32A-F, for securing the garment in a self-retaining, wrapped configuration around the limb. Desirably, the garment 14 is sized and shaped to fit the limb in a manner that avoids wasted energy typically associated with inflating a loosely fitted garment. Any suitable approach of determining fit of the garment 14 and accordingly adjusting the fasteners 30A-F, 32A-F is within the scope of the invention. Such approaches may include, but are not limited to, simple user measurements such as inserting a finger between the garment 14 and the limb to check for fit, and more complex, sensor-based fitting mechanisms formed on the garment itself.

FIG. 2A illustrates the fasteners as hook (30A-F) and loop (32A-F) tabs for this purpose. FIG. 2B shows the garment 14 in a wrapped configuration on a leg of a patient, and illustrates the fasteners 30A-F, 32A-F during use. Alternatively, buckles and/or hook and loop wraps may be employed. Any design of the fasteners 30A-F, 32A-F is within the scope of the invention. In the exemplary embodiment illustrated in FIGS. 2A and 2B, garment 14 comprises four inflatable bladders 36-39 (referred to as bladders 18a-n in FIG. 1) for selectively applying compression to the limb upon inflation. Any number, shape, and configuration of the inflatable bladders 36-39 is within the scope of the invention.

Referring again to FIG. 1, the compression control unit 26 is operable for controlling operation of the compression system 10. A pump 42 of the unit 26 connects to a fluid supply 46 and provides a fluid (e.g., compressed air) to the bladders 18a-n via connection tubing. Specifically, an outlet port 50 of the pump 46 controls fluid delivery to the bladders 18a-n. As is typically known for IPC systems, bladders 18a-n undergo alternate inflation and deflation cycles to provide intermittent compression. The control unit 26 also comprises a processor 54 for monitoring VRT and determining patient compliance (described below), though more than one processor may be employed without departing from the scope of the invention. Processor 54 in general is operable to execute the various functions of the compression control unit described above and hereafter. For example, processor 54 executes software instructions for monitoring sensor 22 and determining VRT and for incrementing the active therapy time accordingly. Moreover, processor 54 is further configured for controlling operation of pump 42 and port 50 during operation. The pressure transducer or sensor 22 is coupled via connection tubing to one of the bladders, bladder 18b in the illustrated embodiment, for monitoring pressure in the bladder 18b. Sensor 22 is preferably coupled to port 50, and in turn coupled to bladder 18b via the same connection tubing as used by pump 42. Alternative connection means are possible as well. The monitored pressure may be employed to determine venous refill time, or VRT, of the limb during a VRT mode of the control unit 26. Referring to FIGS. 3A-3E, processor 54 is configured to execute computer-executable instructions for pressurizing the bladder 18b, for example, to determine a customized venous refill time for the bladder. In an embodiment, when it is desired to determine the venous refill time for the patient, control unit 26 permits bladder 18b to reach a compression pressure and then causes it to depressurize until the pressure in that particular bladder reaches a lower value,. The computer-executable instructions for determining the venous refill time comprise pressurizing the bladder 18b to a first compression pressure (e.g., 20 mm Hg) to move the blood in the leg from a region (e.g., calf) underlying the bladder. After pressurizing the bladder 18b to the first compression pressure, the pressure in the bladder is reduced to a refill pressure (e.g., 10 mm Hg) to allow the blood to reenter the region of the limb underlying the bladder (after approximately 2.5 seconds of depressurization).

The pressure in the bladder 18b is then sensed by the pressure transducer 22 until it is determined that blood flow has been completely restored to the region of the limb underlying the bladder. The time elapsed to restore blood flow is characterized as a first venous refill time $t_1$ and is stored by the controller 26. The bladder 18b is then pressurized to a second compression pressure (e.g., 30 mm Hg) and the same process is performed as was performed for the first compression pressure, resulting in a second venous refill time $t_2$. The bladder 18b can then be pressurized to even more compression pressures (e.g., 45, 60 and 75 mm Hg) and the process performed for the first and second compression pressures can be repeated for each pressure level to produce venous refill times $t_3$, $t_4$, $t_5$, $t_n$, for each additional pressure level. It is understood that pressure amounts other than those described above and shown in FIGS. 3A-3E can be used in the venous refill process without departing from the scope of the invention. Additionally, the venous refill process at each pressure level can be performed multiple times to produce multiple venous refill times for each pressure level.

Alternatively, the bladder under inspection could be permitted to depressurize for a predetermined period of time, or to depressurize fully and then be repressurized until the pressure reaches the predetermined value, for example, 10 mm Hg. The pressure transducer 22 senses the pressure in bladder 18*b* for a time sufficient to allow the venous system in the limb to refill, i.e., engorge with blood again. The pressure as sensed by pressure transducer 22 rises as the limb expands upon filling with blood and reaches a generally steady state when the leg has refilled. The time between the start of depressurizing the bladder 18*b* and when this plateau occurs is measured to be the VRT.

Figure 4:
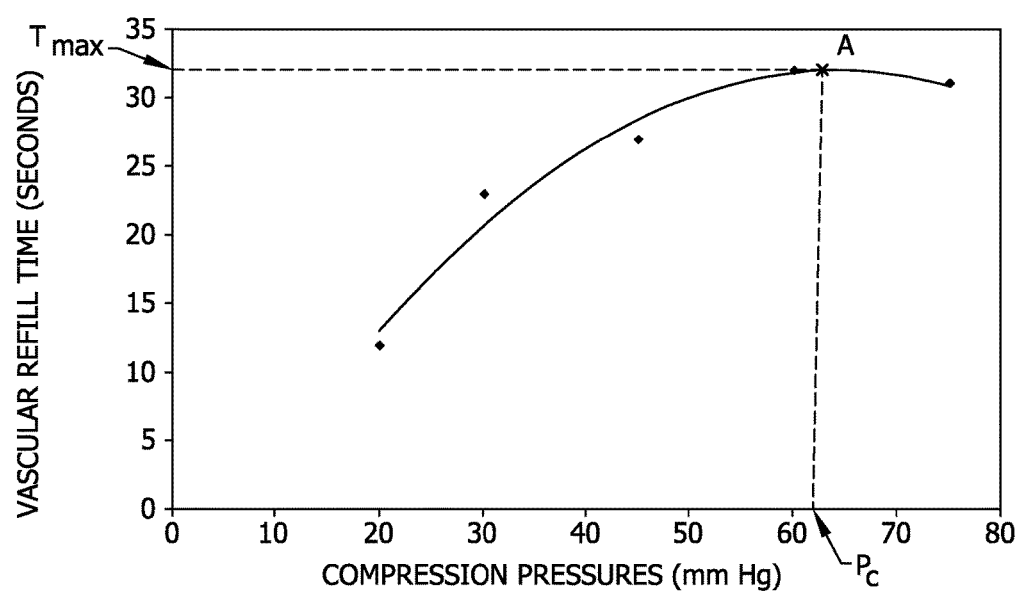
FIG. 4 is a graph illustrating an exemplary customized venous refill determination based on the pressure profiles in FIGS. 3A-3E.

For example, using the determined venous refill times $t_1$-$t_n$, the processor 54 determines a customized compression pressure by plotting the venous refill times for each selected pressure level on a graph as shown in FIG. 4 and fitting a best fit line to the plot using standard linear regression analysis. The apex A of the best fit line corresponds to a customized compression pressure $P_c$ for producing a maximum venous refill time $T_{max}$. The determined compression level $P_c$ and refill time Tmax are then incorporated into the compression therapy of the limb wherein the bladder 18*b* in the garment, or sleeve, 14 is repeatedly pressurized to the customized compression pressure $P_c$ maintained at the customized compression pressure for a period of time and subsequently reduced to the refill pressure for the determined maximum refill time $T_{max}$ to facilitate blood circulation in the limb.

In the instance where multiple venous refill times are recorded for each selected compression pressure level, the refill times are averaged by the processor 54 to produce an average value for the given pressure level. These average values are then plotted and a best fit line is fit to the plot of the average values and the customized compression pressure and maximum venous refill time are extrapolated from the plot in the same manner as described above. If the garment 14 includes multiple bladders (e.g., ankle, calf and thigh bladders as shown in FIGS. 2A and 2B), the controller 26 can be configured to operate the IPC device 10 to apply sequential compression therapy to the limb using the customized pressure and maximum refill time.

In an additional or alternative embodiment, each time control unit 26 determines VRT, it cycles (i.e., inflates and deflates) bladder 18*b* through several values of compression pressure to obtain a corresponding VRT value for each value of compression pressure. The control unit 26 then calculates a maximum VRT, or $V_{max}$. $V_{max}$ is ascertained by determining a best fit between the compression pressure values and the corresponding VRT values via any suitable fitting method (e.g., linear regression analysis). Specifically, a maxima of the best fit designated as $V_{max}$. Desirably, instead of using individual VRT values, multiple VRTs are recorded and averaged for each compression pressure to provide an average VRT value for each compression pressure value.

A custom compression pressure $P_c$ is then determined corresponding to $V_{max}$ and is designated as a target compression pressure of the compression therapy regimen of bladder 18*b*.

After applying compression therapy to the limb for a period of time the process for determining the customized compression pressure and maximum venous refill time can be repeated to determine new values. Additionally or alternatively, memory in the controller 26 can record the venous refill times sensed by the pressure transducer 22 during the compression therapy and, for example, average the recorded values to adjust the time between consecutive pressurizations of the bladder 18*b* based on the averaged refill times. These two processes ensure that the compression therapy being delivered to the limb adapts to the changing characteristics of the limb so that a customized compression therapy is delivered to the limb through the duration of the compression therapy.

As described above, processor 54 of the control unit 26 is responsive to the output signal of pressure sensor 22 for determining the VRT as described above. The unit 26 is further operable to monitor the determined VRT over time. Any aspect of the measured VRT may be monitored, including, but not limited to: individual VRT values, average VRT within a specific time window, average VRT within a moving time window. Variations in VRT over multiple VRT measurements and/or compressive cycles, the steady state pressure achieved during the VRT measurement, any compression cycle parameter, and so on.

Most patients have a normal VRT between 40-50 seconds for leg measurements, with inanimate leg forms generating VRT values as low as 30 seconds. A VRT of approximately 30 seconds is also typically observed when the garment 14 is not in use by the patient. Hence, the monitored VRT may be used for determining whether the patient is using the garment 14. Accordingly, in a preferred embodiment, control unit 26 stores and increments an active therapy time when the monitored VRT either falls within a normal range (e.g., 30-60 seconds), or simply exceeds a predetermined threshold (e.g., 30 seconds), both of which are indicative of normal usage of compression system 10. In this manner, the value of active therapy time is a measure of the patient wearing garment 14 and its sequential inflation and deflation. Alternatively, active therapy time is the cumulative time of controller operation during which the patient is deemed compliant.

In another embodiment, control unit 26 comprises an alarm 58 indicating to a user when the monitored VRT falls below the predetermined threshold. At this point, processor 54 ceases incrementing the active therapy time until further action is taken. The alarm 58 may be one or more of an audio alarm and a visual alarm. The user, typically the patient or a clinician monitoring the patient, may respond to the alarm 58 by indicating that the patient is indeed compliant, such as the case where a patient changes positions and causes an intermittent dip in monitored VRT. In other words, the user overrides the alarm. The therapy time would then continue to be incremented.

When the clinician indicates continued compliance by overriding the alarm 58 triggered by a lower VRT value (than the predetermined threshold), control unit 26 resets or revises the predetermined threshold value to the lower VRT value measured at the time of the override. In this manner, alarm 58 will not be triggered again until the monitored VRT dips to the revised threshold value. This prevents alarm 58 from becoming bothersome in the event the patient has or often achieves a lower VRT value for a justifiable reason such as unique physiology, posture, etc.

Alternatively, in response to alarm 58, the clinician may determine that the patient is not wearing the garment 14 and is therefore not being compliant with the compression regimen. The clinician may respond by turning off control unit 26, at which point the therapy time ceases to increment. The therapy time may advantageously be stored in a memory 62, external or internal to processor 54, for continued measurement the next time the control unit 26 is started.

In yet another embodiment, control unit 26 has a configurable option that allows therapy time to continue to increment despite the monitored VRT falling below the predetermined threshold. In this embodiment, accumulation of therapy time is halted only when a clinician turns off the control unit 26, in response to alarm 58 or otherwise. Continuing to increment the therapy timer in this manner permits the clinician to closely track an operation time of control unit 26, referred to hereafter simply as controller operation time. This embodiment is beneficial when monitoring patients with uncharacteristically low VRT, such as those suffering from venous insufficiency, for example. In such a patient, low VRT measurements may erroneously indicate non-compliance during use. The clinician with knowledge of the patient's condition can then manually control accumulation of therapy time.

Determining patient compliance from active therapy time may be carried out in a number of ways. In one embodiment, patient compliance is simply the therapy time value. In another embodiment, patient compliance is specified as a ratio between active therapy time and controller operation time.

In another embodiment, a shift time is monitored and has a specified value, such as 24 hours. Compliance is specified as a ratio between active therapy time and shift time. Once monitoring is initiated, both active therapy time and shift time are continually evaluated. When the operation time of the controller reaches the shift time (i.e., operation time=24 hours), the compliance measurement is limited to a rolling 24-hour (shift time) window. At any time point thereafter, active therapy time and hence compliance is accounted for only over the last 24 hours of operation. Desirably, shift time is programmable and resettable by a user. In this manner, a clinician or other healthcare provider can specify his or her own shift time, and then observe how long the patient has been compliant during the shift.

Figure 5A:
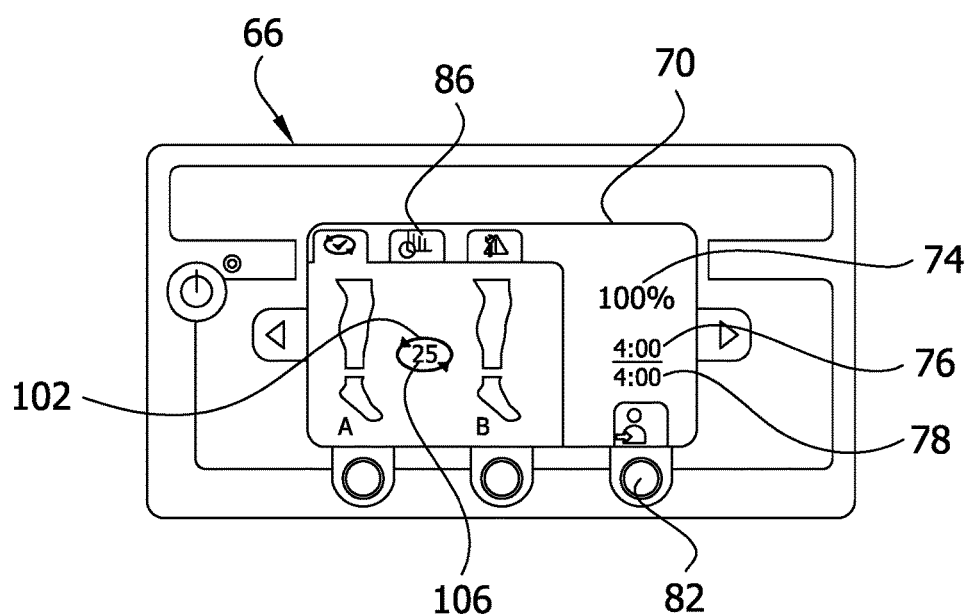
FIG. 5A is an interface of the control unit according to an embodiment of the invention.

The control unit 26 further includes a controller interface 66. A display 70 of the interface 66, as illustrated in FIG. 5A, displays patient compliance as a percentage 74, wherein the percentage is evaluated as a ratio between the displayed active therapy time 76 and the displayed shift time 78. The interface 66 includes a RESET option 82 for resetting the timers. The display 70 also illustrates a VRT indicator 102 and a VRT value 106.

Figure 5B:
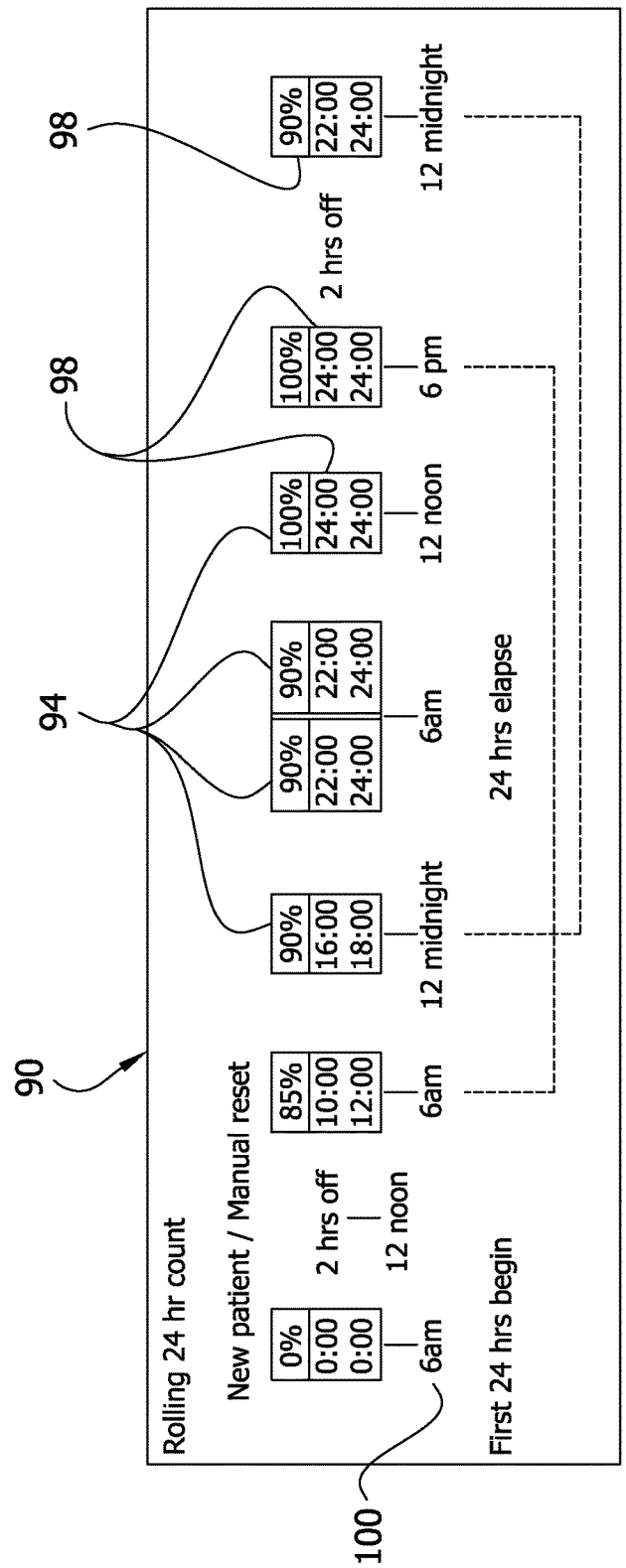
FIG. 5B is an exemplary display of patient compliance according to an embodiment of the invention.

A user may further access a Compliance Graph 90 (see FIG. 5B) via a graph option 86 of the interface 66. Specifically, FIG. 5B illustrates a rolling 24-hour window for monitoring compliance and shows a percentage compliance 94. The exemplary user interface of FIG. 5B displays the percentage compliance 94 along with a boxed representation of the therapy time and shift time (denoted together by the reference character 98) at various time points. The timers are reset at time point 100, and monitored thereafter. In this example, compliance is approximately 90% for the first 24 hours (6 am-6 am), 100% for the 6 pm-6 pm slot, and 90% for the 12 midnight-12 midnight slot. Other means of displaying compliance and the various timers are within the scope of the invention.

Figure 6:
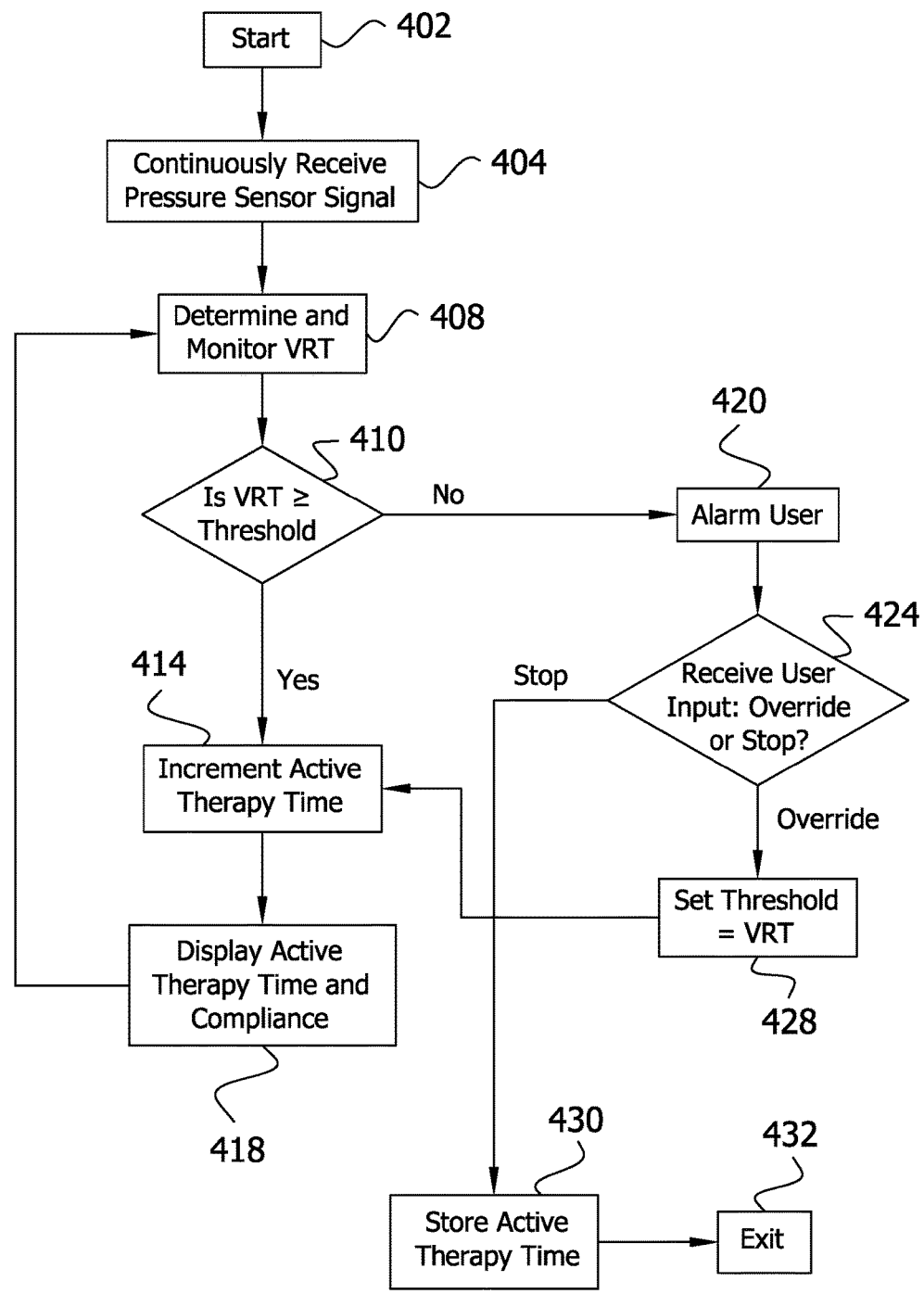
FIG. 6 is an exemplary flowchart for monitoring compliance according to an embodiment of the invention.

According to aspects of the invention, a method of monitoring patient compliance is generally illustrated in FIG. 6 in the form of an exemplary flow diagram. Compliance monitoring is initiated or reset at 402. At 404, a signal is continuously received from the pressure sensor 22 coupled to the bladder 18b. The signal is a function of bladder pressure, and is further indicative of a change of girth of the limb or body part of the patient. The venous refill time or VRT of the limb is determined and monitored as a function of the received signal at 408. At 410, a determination is made whether the monitored VRT exceeds the predetermined threshold. If this is the case, the active therapy time is incremented at 414. The active therapy time and compliance is displayed to the user at 418.

If, at 410, the monitored VRT does not exceed the threshold, the alarm 58 is initiated at 420. At 424, the user responds by either overriding the alarm 58 or stopping the control unit 26. If the user chooses to override the alarm, 58, the threshold is set to the monitored VRT value at 428, and the active therapy time continues to increment as described above. If the user chooses at 424 to stop the control unit 26, the active therapy time is stored to memory 62 at 430, and the control unit 26 shuts down at 432.

Figure 7:
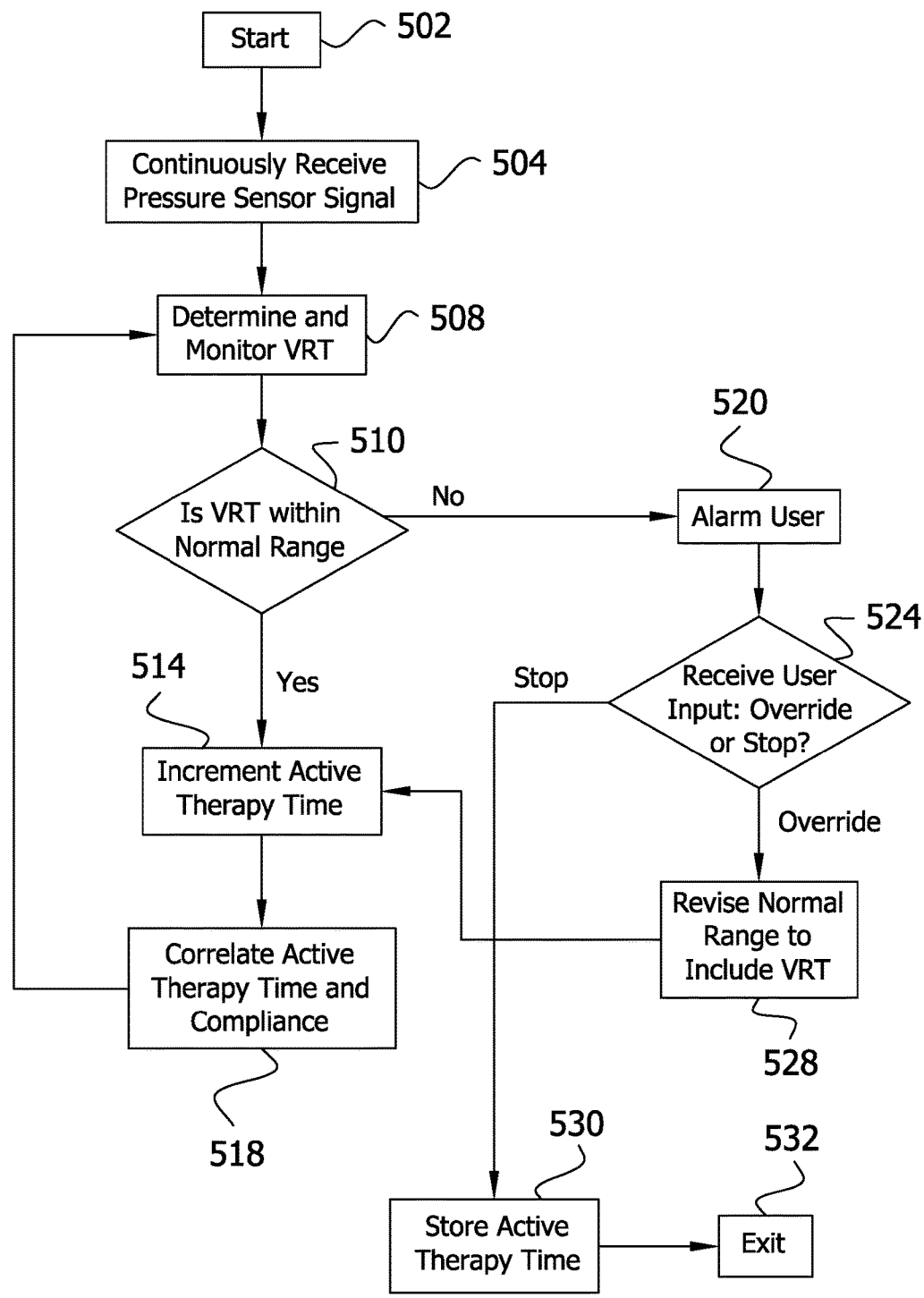
FIG. 7 is an exemplary flowchart for monitoring compliance according to another embodiment of the invention.

According to further aspects of the invention, a method of monitoring patient compliance is generally illustrated in FIG. 7 in the form of an exemplary flow diagram. Compliance monitoring is initiated or reset at 502. At 504, a signal is continuously received from the pressure sensor 22 coupled to the bladder 18b. The signal is a function of bladder pressure, and is further indicative of a change of girth of the limb or body part of the patient. The venous refill time or VRT of the limb is determined and monitored as a function of the received signal at 508. At 510, a determination is made whether the monitored VRT exceeds the predetermined threshold. If this is the case, the active therapy time is incremented at 514. The active therapy time is correlated to compliance, and may further be displayed to the user, at 518.

If, at 510, the monitored VRT does not exceed the threshold, the alarm 58 is initiated at 520. At 524, the user responds by either overriding the alarm 58 or stopping the control unit 26. If the user chooses to override the alarm, 58, the threshold is set to the monitored VRT value at 528, and the active therapy time continues to increment as described above. If the user chooses at 524 to stop the control unit 26, the active therapy time is stored to memory 62 at 530, and the control unit 26 shuts down at 532.

Having described aspects of the invention in detail, it will be apparent that modifications and variations are possible without departing from the scope of the invention defined in the appended claims. For example, an upper predetermined threshold (e.g., 60 seconds) of monitored VRT may be defined that triggers the alarm as well. In other words, the alarm may be triggered above and below a predetermined range of normal VRT values, typically 30-60 seconds. The upper predetermined threshold may be resettable as well. Additionally, more than one inflation bladder may be connected to a different pressure sensor each, and the pressure readings from several pressure sensors may then be combined in any way possible to determine VRT and/or compliance.

The compliance percentage may, in addition to being indicated numerically as illustrated, also be displayed via graphical elements such as a pie chart (not shown). Interface 66 is desirably an integrated display with associated soft keys as illustrated, allowing the user to select and browse various elements described above using the soft keys. However, other constructions of the interface 66 are within the scope of the invention.

To improve patient compliance with compression therapy, there is a need for increasing clinician participation while providing the clinician a utility for compliance notification and monitoring. Several requirements must be fulfilled to achieve this goal. The clinician should be notified when compliance is purportedly not being achieved. Further, the clinician should be able to decide whether to deem the patient compliant or not, and adjust compliance parameters to each patient. Finally, the clinician should be able to monitor the duration of compliance for specific time periods, since they are more likely to be concerned with patient compliance during their work shift(s). A user-friendly compliance monitoring interface is provided for this purpose.

Figure 8B:
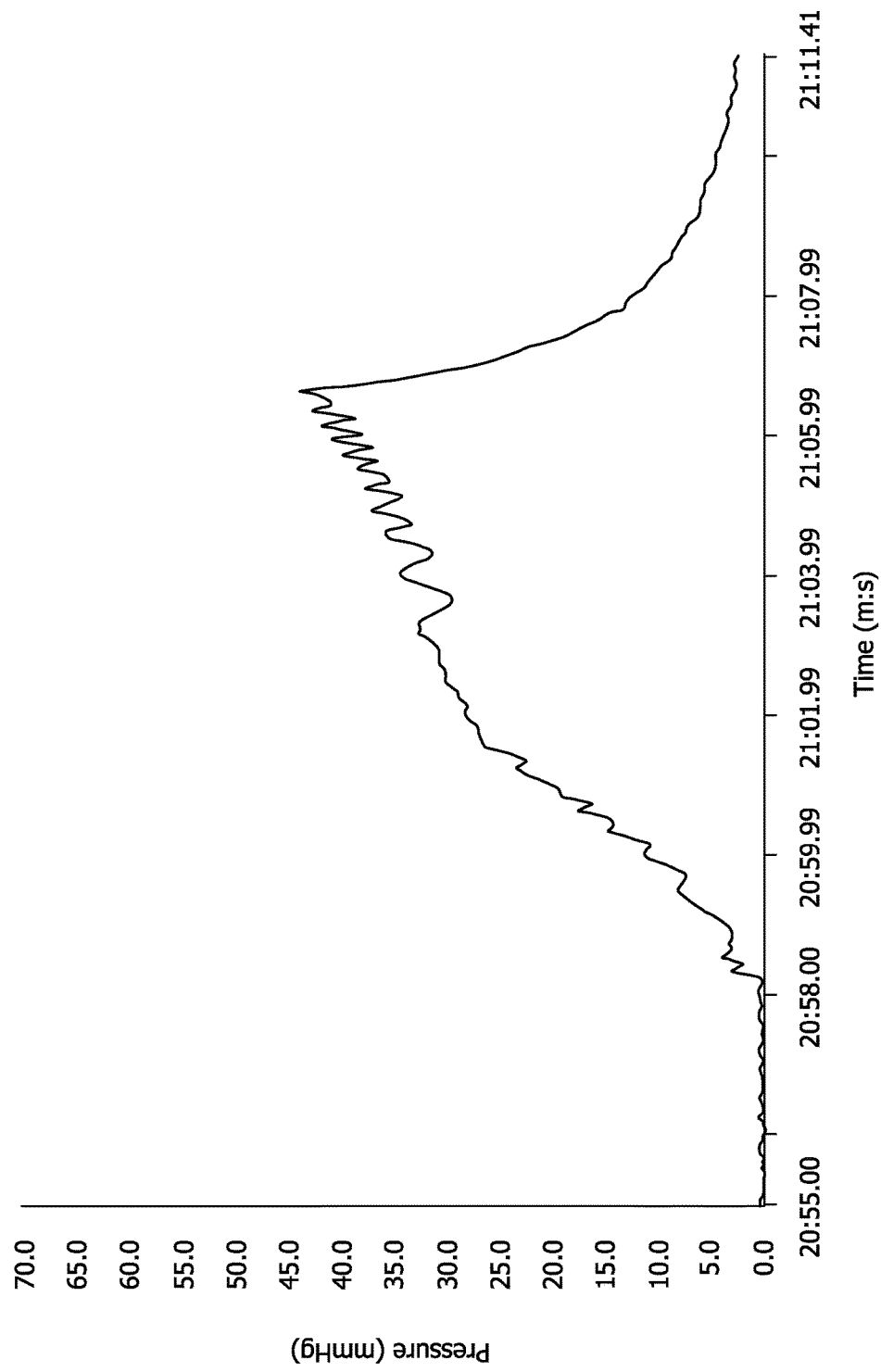
FIG. 8B is a graph illustrating an exemplary pressure cycle of an inflatable bladder when in use.

In view of the above, it will be seen that the several objects of the invention are achieved and other advantageous results attained. FIGS. 8A and 8B illustrate, during operation, a pressure cycle of inflatable bladder 18b. Even when not in use by a patient, bladder 18b reaches pressure values (see FIG. 8A) that are similar to when the bladder 18b is in use by a patient (see FIG. 8B). The difference in the curve peaks is merely 2-3 mmHg for the illustrated case. When monitored by a pressure sensor, the pressure values correspond to internal bladder pressure, and cannot adequately account for actual usage of the garment 14. Pressure profiles for measuring VRT, on the other hand, are determined by reducing bladder pressure to a refill pressure and closing a vent valve (as described above), followed by monitoring pressure increase as blood re-enters the limb. Blood flow to the limb results in expansion of the limb, which forces air out of bladder 18b, back through connecting tubing and onto the sensor 22, which records an increase in pressure. Processor 54 then evaluates the increase in pressure to calculate VRT and determines compliance.

Figure 9A:
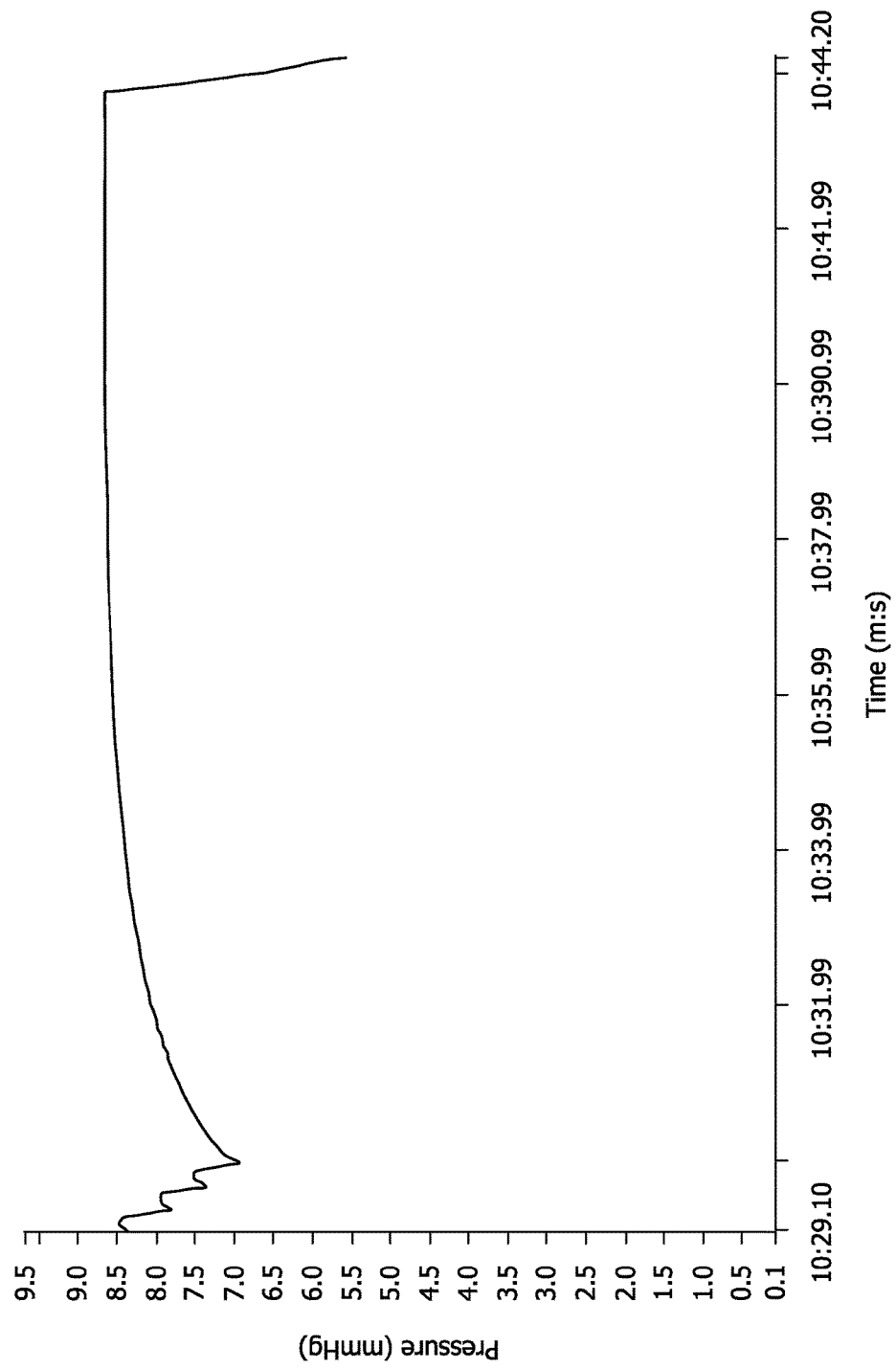
FIG. 9A is a graph illustrating an exemplary pressure profile during venous refill determination of an inflatable bladder when not in use.
Figure 9B:
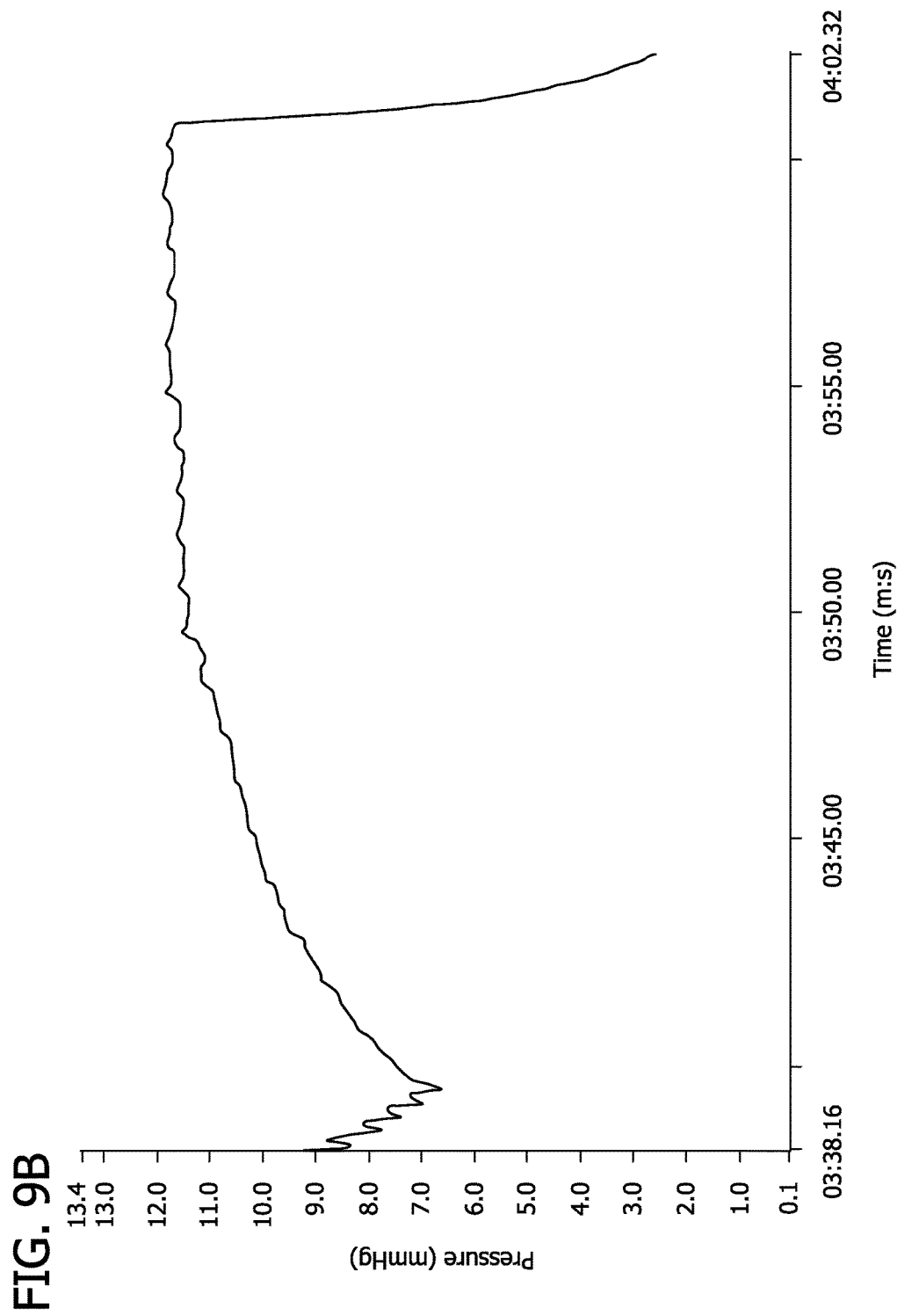
FIG. 9B is a graph illustrating an exemplary pressure profile during venous refill determination of an inflatable bladder when in use.

FIGS. 9A and 9B illustrate the pressure profile as a refill curve of bladder 18b during VRT measurement. The illustrated pressure profile compares two scenarios, namely, a) when garment 14 is not in use by a patient (see FIG. 9A) and b) during use by a patient (see FIG. 9B). When no blood flow is detected such as during non-use, an insignificant increase in pressure is observed, a little less than 2 mmHg for the illustrated case and attributable to pressure stabilization. During use, on the other hand, a pressure change as high as 10 mmHg is observable (approximately 5.5 mmHg for FIG. 9B) in bladder 18b due to distension of the limb.

Embodiments of the invention translate this detectable change in pressure to VRT and for indication of compliance, thereby providing a strong correlation between actual use and estimated compliance.

Additionally, by using the same pressure sensor and output to monitor VRT and usage, a controller is able to determine compliance without requiring additional, cumbersome hardware on the garment itself.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products and methods without departing from the scope of the invention, it is intended that all matter contained in the above description and shown in the accompanying drawings shall be interpreted as illustrative and not in a limiting sense.

What is claimed is:

1. A control unit for monitoring patient compliance with a compression therapy regimen delivered to a body part by inflatable bladders of a compression garment in fluid communication with the control unit, the control unit comprising:
    at least one pressure sensor for detecting pressure in at least one of the inflatable bladders and generating signals corresponding to the measured pressure;
    a pump for pressurizing fluid;
    an outlet port in fluid communication with the pump, said outlet port being configured to connect fluid tubing thereto for selectively delivering pressurized fluid to at least one of the inflatable bladders;
    a memory for storing data;
    one or more processors receiving and responsive to the signals generated by the at least one pressure sensor, the one or more processors being in communication with the memory; and
    computer-executable instructions embodied on a computer readable storage medium, the computer-executable instructions including instructions for causing the one or more processors to:
    determine a characteristic of blood flow in the body part as a function of the received signals; and
    increment a patient compliance timer when the determined blood flow characteristic meets a predetermined standard.

2. The control unit as set forth in claim 1 wherein the instructions for causing the one or more processors to determine a characteristic of blood flow includes instructions to evaluate a pressure profile from the signals generated by the at least one pressure sensor.

3. The control unit as set forth in claim 2 wherein the instructions to evaluate a pressure profile comprise instructions to calculate vascular refill time.

4. The control unit as set forth in claim 3 wherein the instructions to increment a patient compliance timer comprise instructions to increment the patient compliance timer when vascular refill time exceeds a predetermined threshold.

5. The control unit as set forth in claim 1 wherein computer-executable instructions further comprise instructions to cause the one or more processors to activate the pump to pressurize at least one of the inflatable bladders to a first pressure and then to a second pressure less than the first pressure, wherein determining a characteristic of blood flow is a function of signals received from the at least one pressure sensor when the inflatable bladder is at the second pressure.

6. The control unit as set forth in claim 5 wherein the instructions to activate the pump include instructions to depressurize the at least one inflatable bladder from the first pressure to the second pressure.

7. A method of monitoring patient compliance with a compression therapy regimen, said method comprising:
    receiving signals from a pressure sensor coupled to a compression garment, wherein the garment is sized and shaped to be wrapped around substantially a limb of a wearer and comprises one or more selectively inflatable bladders for applying compression to the limb upon inflation, the received signals indicating a pressure in the one or more selectively inflatable bladders, the signals being indicative of a characteristic of blood flow in the limb when the compression garment is wrapped substantially around the limb of the wearer;
    determining the blood flow characteristic as a function of the received signals;
    comparing the blood flow characteristic to a predetermined standard of blood flow characteristics; and
    correlating the blood flow characteristic to patient compliance as a function of said comparing.

8. The method as set forth in claim 7 wherein determining a characteristic of blood flow comprises creating a pressure profile from the signals generated by the pressure sensor.

9. The method as set forth in claim 8 wherein correlating the blood flow characteristic to patient compliance comprises comparing the pressure profile to an expected pressure profile.

10. The method as set forth in claim 9 wherein correlating the blood flow characteristic to patient compliance comprises calculating vascular refill time.

11. The method as set forth in claim 10 further comprising incrementing a patient compliance timer when vascular refill time exceeds a predetermined threshold.

12. The method as set forth in claim 7 further comprising controlling pressure in at least one of the inflatable bladders to a first pressure and then to a second pressure less than the first pressure, wherein determining a characteristic of blood flow is a function of signals received from the pressure sensor when the inflatable bladder is at the second pressure.

13. The method as set forth in claim 12 wherein controlling pressure in at least one of the inflatable bladders includes depressurizing the at least one inflatable bladder from the first pressure to the second pressure.

* * * * *